United States Patent [19]

Kato

[11] Patent Number: 5,199,060

[45] Date of Patent: Mar. 30, 1993

[54] X-RAY PHOTOGRAPHING APPARATUS

[75] Inventor: Kunitaka Kato, Utsunomiya, Japan

[73] Assignee: Kabushiki Kaisha Toshiba, Kawasaki, Japan

[21] Appl. No.: 709,974

[22] Filed: Jun. 4, 1991

[30] Foreign Application Priority Data

Jun. 4, 1990 [JP] Japan .................. 2-144446

[51] Int. Cl.$^5$ ............................................. H05G 1/02
[52] U.S. Cl. .................... 378/196; 378/208; 378/195; 378/176
[58] Field of Search .............. 378/208, 209, 177, 180, 378/195, 196, 198, 176, 19; 5/601

[56] References Cited

U.S. PATENT DOCUMENTS

| 4,363,128 | 12/1982 | Grady et al. | 378/189 |
| 4,501,011 | 2/1985 | Hauck et al. | 378/197 |
| 4,653,083 | 3/1987 | Rossi | 378/197 |
| 4,914,588 | 4/1990 | Schittenhelm | 378/19 |

Primary Examiner—Constantine Hannaher
Assistant Examiner—Don Wong

Attorney, Agent, or Firm—Oblon, Spivak, McClelland, Maier & Neustadt

[57] ABSTRACT

An x-ray photographing apparatus includes a first x-ray image detecting unit having a first x-ray image detection region, a second x-ray image detecting unit arranged in tandem with the first x-ray image detecting unit and having a second x-ray image detection region, and a bed apparatus having a subject placing unit for moving a subject to be examined between the first and second x-ray image detection regions. The first x-ray image detecting unit performs x-ray film photography and fluoroscopy of the lower limbs of a subject to be examined. The second x-ray image detecting unit performs x-ray film photography of the entire region of the lower limbs of the subject. The bed apparatus serves to perform photography of a blood vessel with a contrast medium. The subject placing unit can arbitrarily perform moving and stopping operations between the first and second x-ray image detection region. In addition, the subject placing member can perform a continuous moving operation and a step moving operation between the first and second x-ray image detection regions.

16 Claims, 8 Drawing Sheets

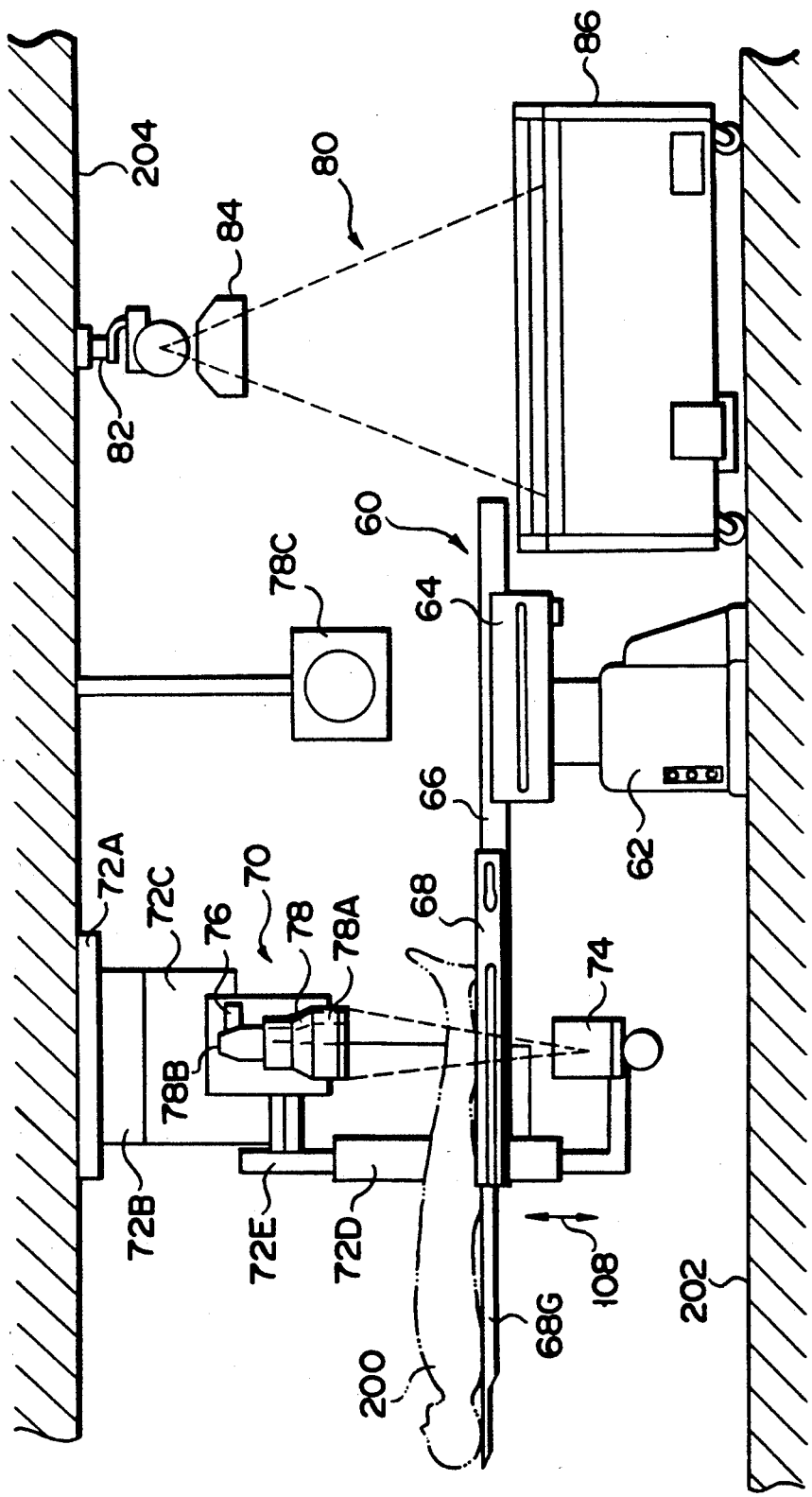
F I G. 4

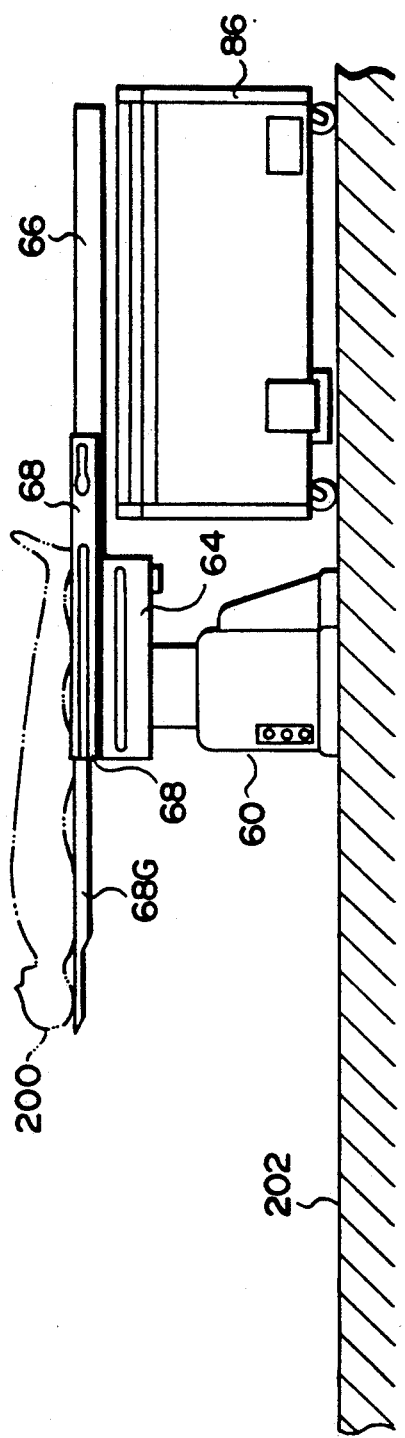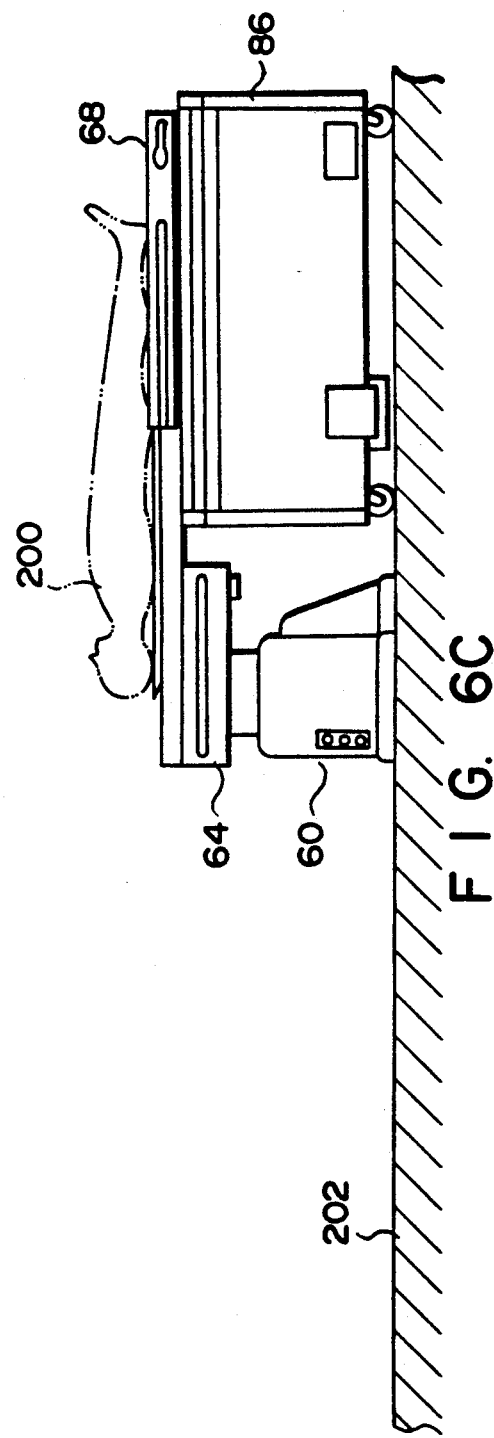

X-RAY PHOTOGRAPHING APPARATUS

BACKGROUND OF THE INVENTION

1. Field of the Invention

The present invention relates to an x-ray photographing apparatus and, more particularly, to an x-ray photographing apparatus including a bed apparatus suitable for photography of circulatory organs, such as blood vessels of lower limbs, by employing various photographing methods.

2. Description of the Related Art

A conventional x-ray photographing apparatus for circulatory organs will be described below with reference to FIG. 1. This circulatory organ x-ray photographing apparatus comprises a photographing system 10 for obtaining an x-ray film image as a photographed image by using a film changer 10A, an x-ray fluoroscopic system 20 for obtaining a fluoroscopic image by using an image intensifier (to be referred to as an I.I. hereinafter) 20A to determine a photographing position, and displaying it on a monitor 20B, and a catheter bed 30 having a top plate unit 30A which can be horizontally moved. In addition to these components, the x-ray photographing apparatus includes various types of electrical units (not shown), e.g., a high-voltage generator and a control unit. In addition, a contrast medium injector (not shown) is arranged near the catheter bed 30.

An example of photography of blood vessels of the lower limbs of a subject to be examined by using the circulatory organ x-ray photographing apparatus will be described below with reference to FIG. 1. While the top plate unit 30A on which a subject 200 is placed is horizontally moved, fluoroscopic x-rays are emitted from an x-ray tube unit 20C of the fluoroscopic system 20. With this operation, a fluoroscopic image of the subject 200 is displayed on the monitor 20B. An operator (not shown) injects a catheter (not shown) into a blood vessel of the subject 200 while observing the fluoroscopic image, thus recognizing a position, in the subject 200, where the distal end of the catheter should reach. Therefore, the operator can move the distal end of the catheter to a predetermined position in the subject while observing the fluoroscopic image. The top plate unit 30A is further moved horizontally to move a portion, of the subject 200, at which the distal end of the catheter is located, to the position of the film change 10A of the photographing system 10. Subsequently, a contrast medium is injected from the contrast medium injector to the portion, of the subject 200, at which the distal end of the catheter is located, through the catheter. At substantially the same time, photographic x-rays are emitted from the x-ray tube unit 10B of the photographing system 10 to form an x-ray photographic image on an x-ray film in the film changer 10A.

The above description is associated with a normal photographing method with respect to a portion of lower limbs. Instead of this normal photographing method, a divisional photographing method is also used to photograph a portion of lower limbs. In this divisional photographing method, it is required that the top plate unit 30A be moved step by step at a relatively high speed. In the case shown in FIG. 1, the number of steps is five. More specifically, while the top plate unit 30A is horizontally moved to sequentially move the subject 200 to positions P1, P2, P3, P4, and P5, photographic x-rays are sequentially emitted from the x-ray tube unit 10B of the photographing system 10, thereby respectively forming x-ray photographic images on different x-ray films which are sequentially changed in the film change 10A. Therefore, a plurality of x-ray photographic images (x-ray film images) of different portions of the lower limbs can be obtained. This photographing operation is equivalent to an operation of photographing the entire region of the lower limbs in divisions.

Instead of using the normal photographing method or the divisional photographing method to photograph a portion of lower limbs, a method of photographing the entire region of lower limbs by one photographing operation is also available. In this photographing method, an elongated x-ray film is used.

FIG. 2 shows an arrangement of an x-ray photographing apparatus for photographing the entire region of lower limbs by using an elongated x-ray film. As shown in FIG. 2, a horizontally movable top plate unit 40A is arranged on a rectangular catheter bed 40. An elongated x-ray film 40B is stored in the catheter bed 40. The x-ray film 40B has a size enough to cover the entire region of the lower limbs of subject 200 to be examined. An x-ray tube unit 50 is fixed to a ceiling.

The entire region of the lower limbs is photographed in the following manner by using the x-ray photographing apparatus having the above-described arrangement. An x-ray radiation region and the position of the elongated x-ray film 40B are caused to coincide with each other by moving either the catheter bed 40 or the x-ray tube unit 50. The top plate unit 40A is moved to locate the lower limb region of the subject 200 immediately above the elongated x-ray film 40B. Subsequently, x-rays are emitted from the x-ray tube unit 50, thus obtaining an x-ray photographic image (x-ray film image) of the entire region of the lower limbs.

In the above-described conventional x-ray photographing apparatus, however, the following problem is posed. When the partial region shown in FIG. 1 is to be photographed in divisions, or when the entire region shown in FIG. 2 is to be collectively photographed by using an elongated film, a special catheter bed must be used in accordance with a photographing method. For this reason, in order to realize an apparatus which can arbitrarily perform a divisional photographing operation and a photographing operation using an elongated film, two catheter beds must be arranged. Therefore, a large space is required to arrange the two catheter beds, and the apparatus is complicated.

SUMMARY OF THE INVENTION

It is an object of the present invention to provide an x-ray photographing apparatus which can perform both divisional and collective photographing operations with respect to a subject to be examined without requiring a large space or a complicated arrangement.

In order to achieve the above object, according to the present invention, there is provided an x-ray photographing apparatus comprising:

first x-ray image detecting means having a first x-ray image detection region;

second x-ray image detecting means arranged in tandem with the first x-ray image detecting means and having a second x-ray image detection region; and a bed apparatus having subject placing means for moving a subject to be examined between the first and second x-ray image detection regions.

In addition, in order to achieve the above object, according to the present invention, there is provided a bed apparatus used for an x-ray photographing apparatus, comprising:

a base member arranged on a floor;

a frame member fixed to an upper surface of the base member;

an intermediate moving member which is arranged on the frame member and can be horizontally moved on the frame member; and a subject placing member which is arranged on an upper surface of the intermediate moving member and can be horizontally moved on the intermediate moving member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a front view of the apparatus in FIG. 3;

FIGS. 6A to 6C are views showing an operation of the apparatus in FIG. 3;

DETAILED DESCRIPTION OF THE PREFERRED EMBODIMENTS

Figure 1:
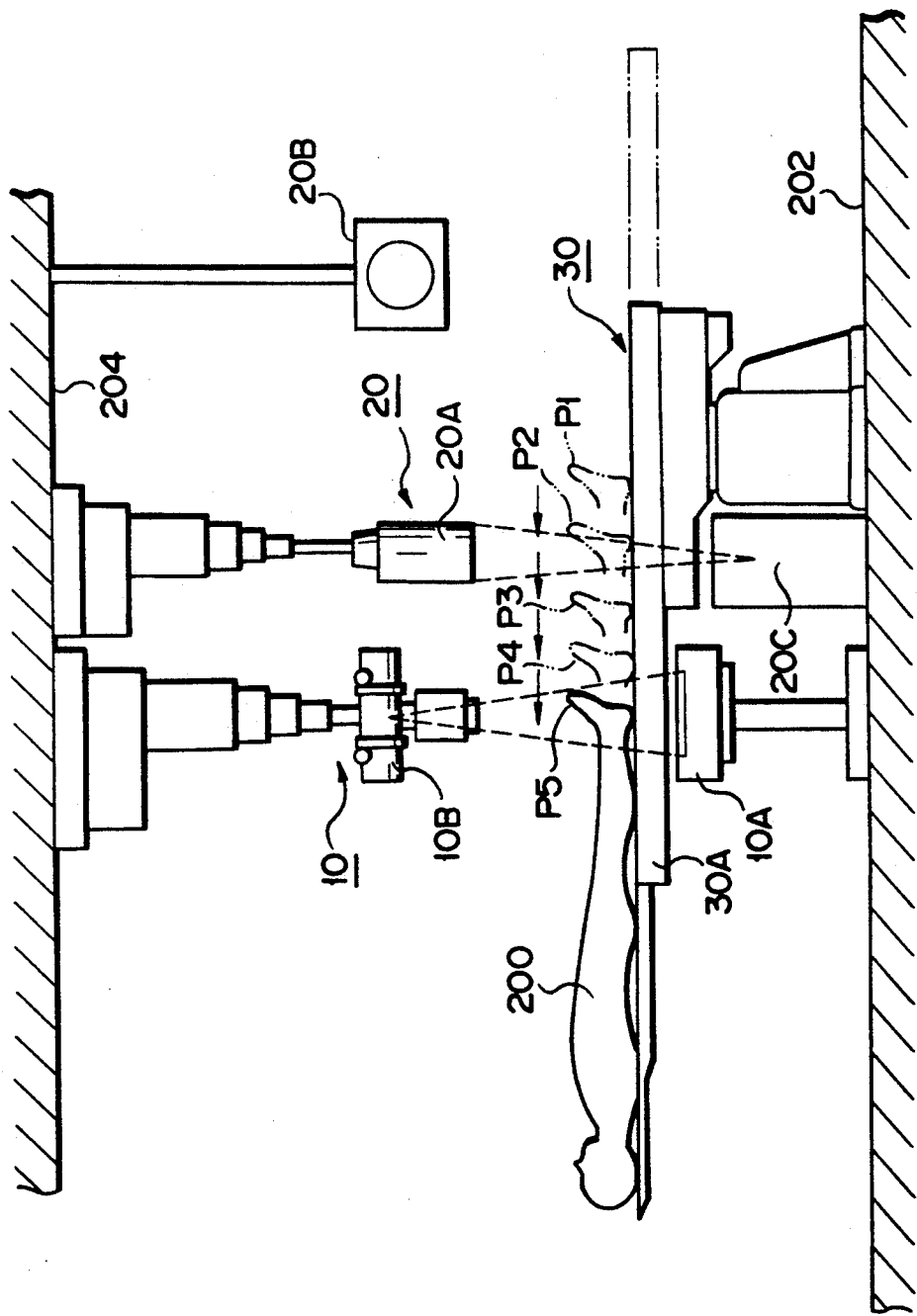
FIG. 1 is a view showing an arrangement of a conventional x-ray photographing apparatus for photographing lower limbs in divisions.

According to an embodiment of the present invention, an x-ray photographing apparatus for photographing lower limbs is disclosed. The x-ray photographing apparatus for lower limbs comprises a catheter bed 60, which is the most important characteristic feature of this embodiment, a C arm unit 70 for obtaining a normal x-ray film image and a fluoroscopic image, and a collective photographing system 80 for obtaining images of an elongated x-ray film. In addition to these components, the x-ray photographing apparatus for lower limbs includes various types of electrical units (not shown), e.g., a high-voltage generator and a control unit. The catheter bed 60 is arranged on a floor 202. The C arm unit 70 is installed on one side (left side in FIG. 3) in the horizontally moving direction of a top plate unit of the catheter 60. The collective photographing system 80 is installed on the other side (right side in FIG. 3) in the horizontally moving direction of the top plate unit of the catheter bed 60. Note that a contrast medium injector (not shown) is arranged near the catheter bed 60.

Figure 5:
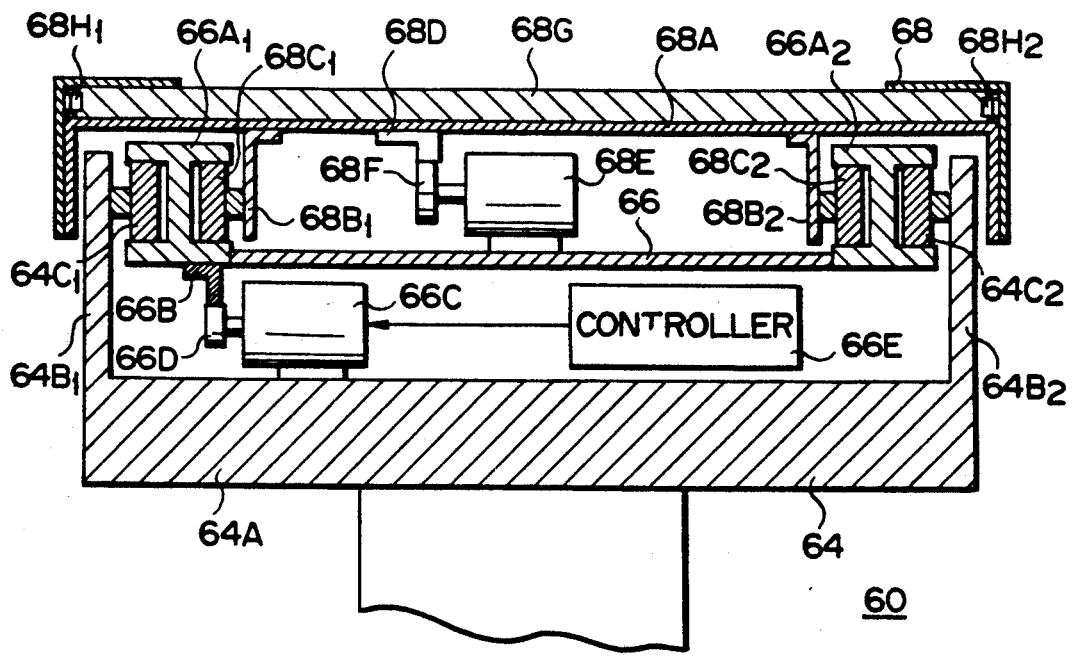
FIG. 5 is a sectional view showing a catheter bed in the apparatus in FIG. 3.

The catheter bed 60 will be described in detail below with reference to FIGS. 3 to 5. A base 62 is vertically fixed on the floor 202. A frame 64 is fixed on the base 62. The frame 64 is constituted by a flat portion 64A and vertical walls 64B1 and 64B2 arranged on both sides of the flat portion 64A. Rollers 64C1 and 64C2 are respectively arranged on the vertical wall 64B1 and 64B2 of the frame 64.

An intermediate moving unit 66 is arranged in the upper part of the flat portion 64A of the frame 64. I-shaped rails 66A1 and 66A2 which respectively receive the rollers 64C1 and 64C2 of the frame 64 are arranged on both sides of the intermediate moving unit 66. A rack gear 66B is arranged on the lower surface of the intermediate moving unit 66. In addition, a motor 66C is fixed to the flat portion 64A of the frame 64. A pinion gear 66D which is meshed with the rack gear 66B is fixed to the rotating shaft of the motor 66C. The motor 66C is controlled by a controller 66E.

Furthermore, a frame 68A of a top plate unit 68 is arranged above the intermediate moving unit 66. Roller support plates 68B1 and 68B2 are arranged below both sides of the frame 68A. Roller 68C1 and 68C2 which are guided by the I-shaped rails 66A1 and 66A2 are respectively arranged on the roller support plates 68B1 and 68B2. Therefore, the I-shaped rails 66A1 and 66A2 respectively receive the rollers 64C1 and 64C2 of the frame 64 on one side, and respectively receive the rollers 68C1 and 68C2 of the top plate unit 68 on the other side. A rack gear 68D is arranged on the lower surface of the frame 68A. A motor 68E is fixed on the upper surface of the intermediate moving unit 66. A pinion gear 68F which is meshed with the rack gear 68D is fixed to the rotating shaft of the motor 68E. The motor 68E is controlled by a controller (not shown). A top plate 68G is arranged on the frame 68A to be horizontally slidable. Solenoid brakes 68H1 and 68H2 are arranged on both sides of the frame 68A to fix the top plate 68G. Each of the solenoid brakes 68H1 and 68H2 is constituted by, e.g., an electromagnet and an iron plate. The electromagnets are arranged on the frame 68A side, whereas the iron plates are arranged at predetermined positions, of the top plate 68G, which correspond to the electromagnets. With this arrangement, by exciting the electromagnets of the solenoid brakes 68H1 and 68H2, the iron plates of the top plates 68G can be attracted by electromagnetic forces, thus inhibiting movement of the top plate 68G. Though not shown, it is possible to replace at least one of the solenoid brakes 68H1 and 68H2 shown in FIGS. 5 and 7 with a manual type brake which is mannually operated by an operator.

According to the catheter bed 60 having such an arrangement, the intermediate moving unit 66 can be horizontally moved with respect to the frame 64. The top plate 68 can be horizontally moved with respect to the intermediate moving unit 66. In addition, the movement amounts, moving speeds, and stop positions of the intermediate moving unit 66 and the top plate unit 68 can be arbitrarily set by the controller 66E for the motor 66C and the controller for the motor 68E, respectively. The intermediate moving unit 66 can be partially stored in the frame 64. The top plate unit 68 can be partially stored in the intermediate moving unit 66. In addition, the intermediate moving unit 66 and the top plate unit 68 of the catheter bed 60 are moved in accordance with one of the following modes: a normal movement mode for obtaining a fluoroscopic image and a normal x-ray film image, a stepping movement mode for divisional photography using a normal x-ray film, a whole body fluoroscopic image mode for obtaining a whole body fluoroscopic image, and a collective photographing mode for collective photography using an elongated x-ray film. Furthermore, in a state wherein the solenoid brakes 68H1 and 68H2 are not driven, the top plate 68G of the top plate unit 68 can be drawn from the frame 68A to a desired position and pushed back.

The C arm unit 70 comprises an arm mechanism 72, an x-ray tube unit 74, a film changer 76 for single-shot photography or divisional photography, and a fluoroscopic system 78 for fluoroscopy. The x-ray tube unit 74, the film changer 76, and the fluoroscopic system 78 are mounted on the arm mechanism 72. The arm mechanism 72 comprises a rail mechanism 72A fixed to a ceiling 204, a base 72B arranged on the rail mechanism 72A, a column 72C fixed to the base 72B, an arm base 72D fixed to the column 72C, and a C arm 72E arranged on the arm base 72D. The base 72B can be moved on the rail mechanism 72A. The column 72C is vertically extendible and can be rotated about its axis. The arm base 73D can be rotated in a direction indicated by reference numeral 106. The C arm 72E can be slid in a direction indicated by reference numeral 108. The x-ray tube unit 74 is attached to one end of the C arm 72E. The film changer 76 and the fluoroscopic system 78 are attached to the other end of the C arm 72E through a switching mechanism (not shown). The fluoroscopic system 78 is constituted by an I.I. 78A, a TV camera 78B, an image processor (not shown), and a TV monitor 78C. By operating the switching mechanic, the x-ray incident surfaces of the film changer 5 76 and the I.I. 78A can be arbitrarily caused to oppose the x-ray emission port of the x-ray tube unit 74. The x-ray tube unit 74 can emit x-rays for obtaining a normal x-ray film image and for obtaining a fluoroscopic image.

According to the C arm unit 70 having such an arrangement, a normal x-ray film image and a fluoroscopic image of the same portion of a subject to be examined can be obtained without moving the subject. In addition, normal x-ray film images and fluoroscopic images of the same portion of the subject in various directions can be obtained without moving the subject.

The collective photographing system 80 comprises an x-ray tube support arm 82 fixed to the ceiling 204, an x-ray tube unit 84, supported on the x-ray tube support arm 82, for emitting x-rays for photography, and an elongated film changer 86 which is arranged on the floor 202 and has an elongated x-ray film stored therein.

An operation of the x-ray photographing apparatus for lower limbs according to this embodiment will be described below. The apparatus of this embodiment is characterized by an operation of the catheter bed 60. As described above, the intermediate moving unit 66 and the top plate unit 68 of the catheter bed 60 are moved in accordance with any one of the normal movement mode, the stepping movement mode, the whole body fluoroscopic image mode, and the collective photographing mode. In this case, the subject 200 is placed on the top plate 78G of the catheter bed 60 in an initial state. Note that the initial state of the catheter bed 60 is a state in which the intermediate moving unit 66 and the top plate unit 68 are stored in the frame 64.

In the normal movement mode, the x-ray photographing apparatus is operated in the following manner. In order to roughly position a portion of the lower limbs of the subject 200 between the arm portions of the C arm 72E of the C arm unit 70, either or both of the intermediate moving unit 66 and the top plate unit 68 are moved toward the C arm unit 70, i.e., the left side in FIG. 3. The x-ray tube unit 74 and the fluoroscopic system 78 are operated to display a fluoroscopic image on the monitor 78C. With this operation, an operator (doctor) can observe the fluoroscopic image. Subsequently, the top plate unit 68 is moved to display a fluoroscopic image of a portion, of the lower limbs of the subject 200, where the distal end of a catheter is to reach. With this operation, the operator (doctor) can observe the fluoroscopic image of the target portion, of the lower limbs of the subject 200, where the catheter distal end is to reach. In this state, the catheter is injected in a target blood vessel in the subject 200 and to cause the catheter distal end to reach the target portion. Thereafter, a contrast medium is injected to the target portion by using the catheter and the contrast medium injector. The switching mechanism is then operated to cause the x-ray incidence surfaces of the film changer 76 to oppose the x-ray emission port of the x-ray tube unit 74. When the x-ray tube unit 74 and the film changer 76 are operated, a normal x-ray film image by single-shot photography can be obtained. This state will be easily understood by referring to FIGS. 6A and 6B.

In the stepping motor movement mode, the x-ray photographing apparatus is operated in the following manner. In contrast to the above-described normal movement mode designed for single-shot photography, the stepping movement mode is designed to intermittently and horizontally move either or both of the intermediate moving unit 66 and the top plate unit 68 at high speed, as shown in FIG. 1, after a contrast medium is injected. The x-ray tube unit 74 and the film changer 76 are operated at every stop position of this intermittent movement so as to perform x-ray film photography of different regions of the lower limbs, thereby realizing divisional photography.

In the whole body fluoroscopic image mode, the x-ray photographing apparatus is operated in the following manner. In order to obtain a fluoroscopic image of the whole lower limbs or the whole body of the subject 200 with or without a contrast medium, the x-ray tube unit 74 and the fluoroscopic system 78 are operated while either or both of the intermediate moving unit 66 and the top plate unit 68 are moved toward the C arm unit 70, i.e., the left side in FIG. 3. As a result, a fluoroscopic image is displayed on the monitor 78C. With this operation, the operator (doctor) can observe the fluoroscopic image of the whole lower limbs or the whole body. This image may be converted into a digital image to be stored in a storage unit.

In the collective photographing mode, the x-ray photographing apparatus is operated in the following manner. As shown in FIG. 6C, in order to obtain an x-ray film image of the whole lower limbs of the subject 200 with or without a contrast medium, the intermediate moving unit 66 and the top plate unit 68 in the initial state are moved toward the collective photographing system 80, i.e., the right side in FIG. 6C. Subsequently, the x-ray tube unit 84 and the elongated film changer 86 of the collective photographing system 80 are operated to perform x-ray film photography of the whole lower limbs, thus realizing collective photography of the entire region of the lower limbs.

Figure 6A:
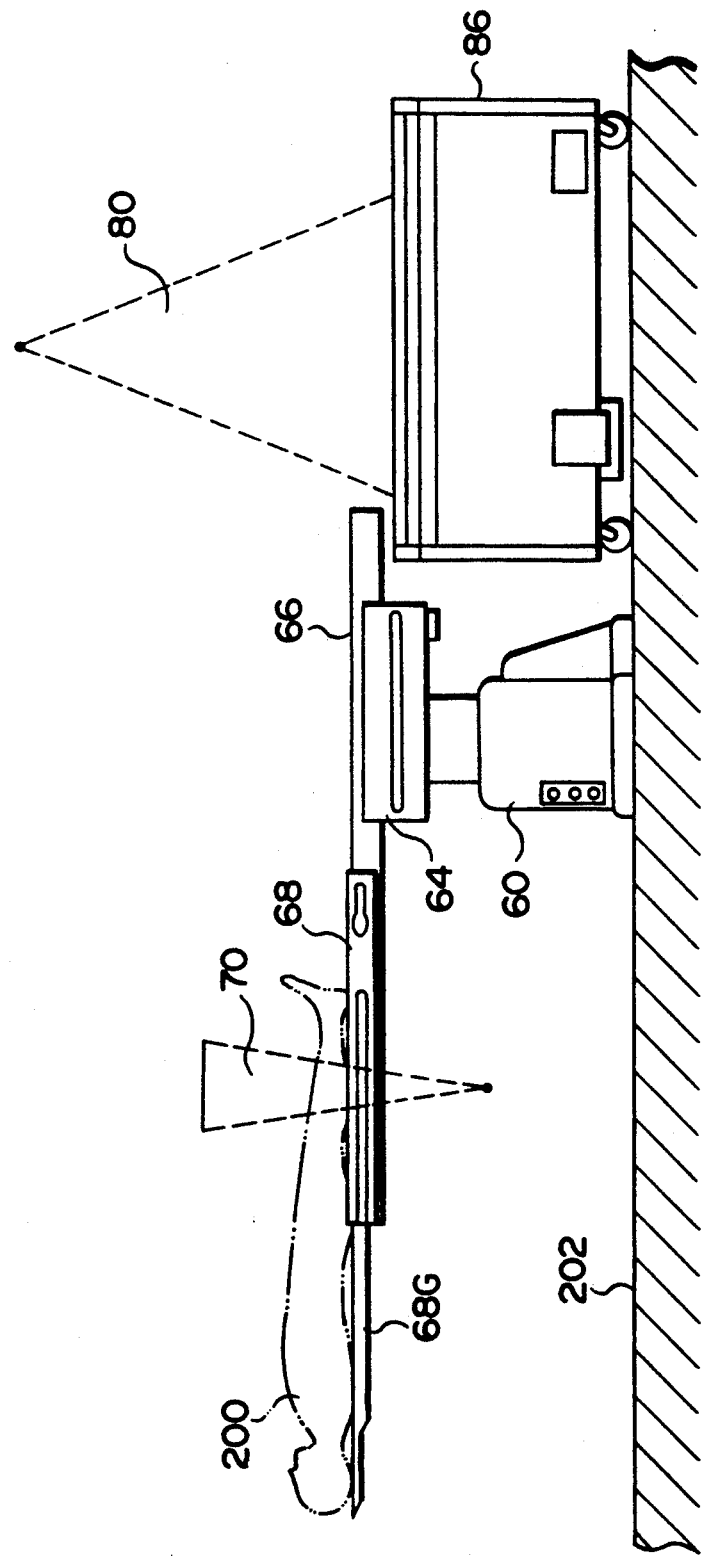

FIG. 6A shows a case wherein the intermediate moving unit 66 and the top plate unit 68 are moved toward the C arm unit 70, i.e., the left side in FIG. 6A. In this case, the top plate 68G is drawn from the top plate unit 68. FIG. 6B shows a case wherein the intermediate moving unit 66 is moved toward the collective photographing system 80, i.e., the right side in FIG. 6, and the top plate unit 68 is moved to the C arm unit 70, i.e., the left side in FIG. 6B. In this case, the top plate 68G is drawn from the top plate unit 68. FIG. 6C shows a case wherein the intermediate moving unit 66 and the top plate unit 68 are moved to the collective photographing system 80, i.e., the right side in FIG. 6C. In this case, the top plate 68G is also drawn from the top plate unit 68. A step photographing operation (divisional photographing operation) can be performed when the state shown in FIG. 6B is shifted to the state shown in FIG. 6A, or the state shown in FIG. 6A is shifted to the sate shown in FIG. 6B.

Figure 7:
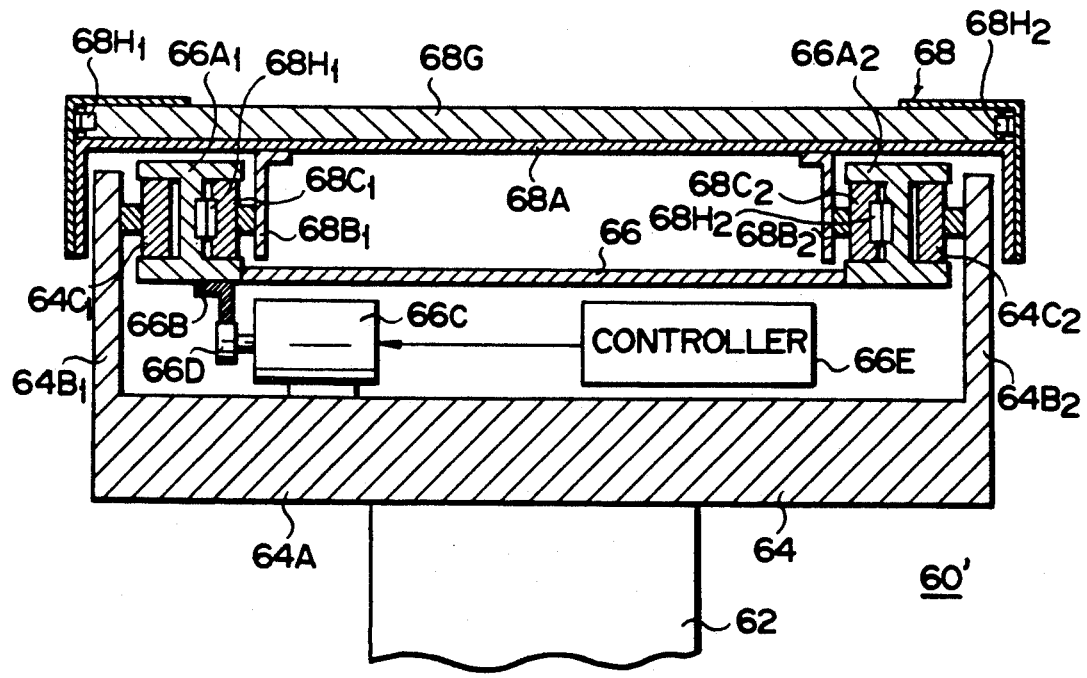
FIG. 7 is a sectional view showing another example of a catheter bed in the apparatus in FIG. 3.

A catheter bed 60' having an arrangement different from that shown in FIG. 5 will be described below with reference to FIG. 7. In this catheter bed 60', the rack gear 68D, the motor 68E, and the pinion gear 68F shown in FIG. 5 are omitted, and solenoid brakes 68H1 and 68H2 are newly arranged between I-shaped rails 66A1 and 66A2 and rollers 68C1 and 68C2 of a top plate unit 68.

According to the catheter bed 60' having such an arrangement, when the solenoid brakes 68H1 and 68H2 are driven, an intermediate moving unit 66 and the top plate unit 68 are integrated with each other. In each operation mode described above, therefore, the intermediate moving unit 66 and the top plate unit 68 can be horizontally moved together. When the solenoid brakes 68H1 and 68H2 are not driven, the top plate unit 68 can be manually pulled out/pushed back from/to the intermediate moving unit 66. Clinically, there is not much necessity to electrically move the top plate unit 68. Therefore, in this embodiment, while clinical requirements are satisfied, a reduction in cost is realized.

Figure 2:
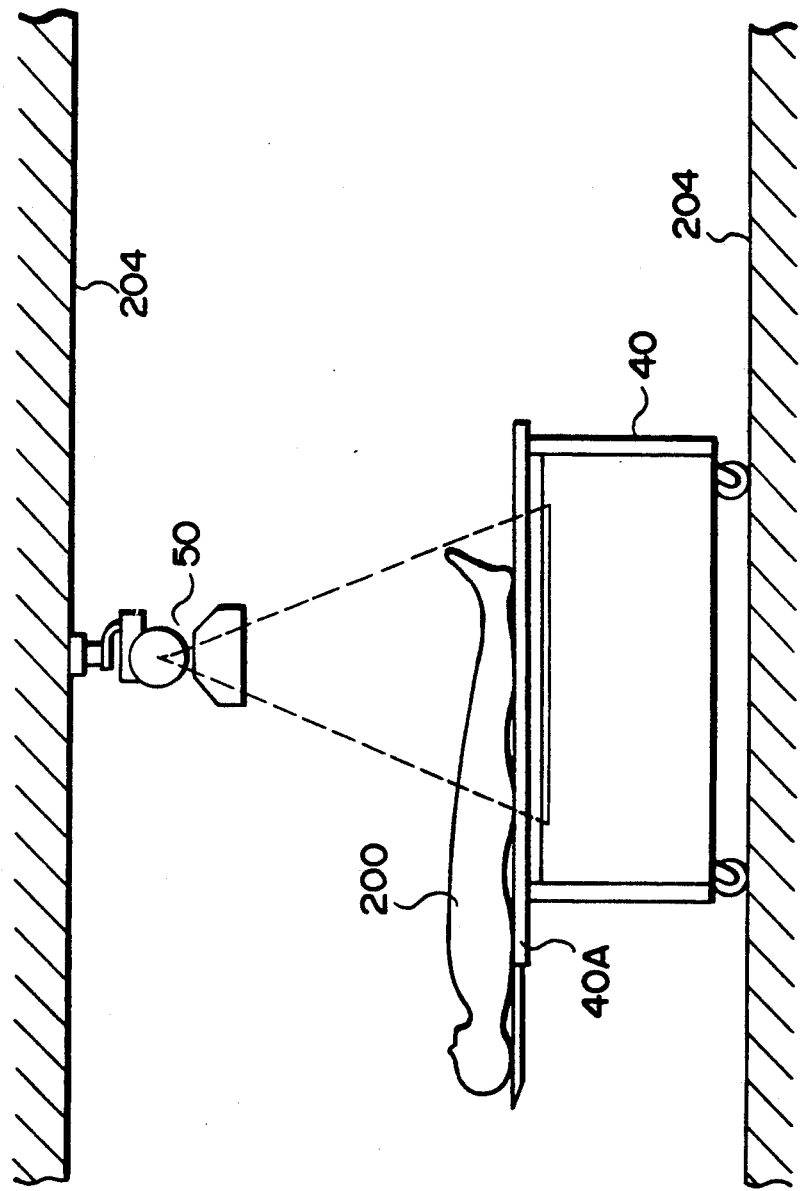
FIG. 2 is a view showing an arrangement of a conventional x-ray photographing apparatus for collectively photographing the entire region of lower limbs.
Figure 8:
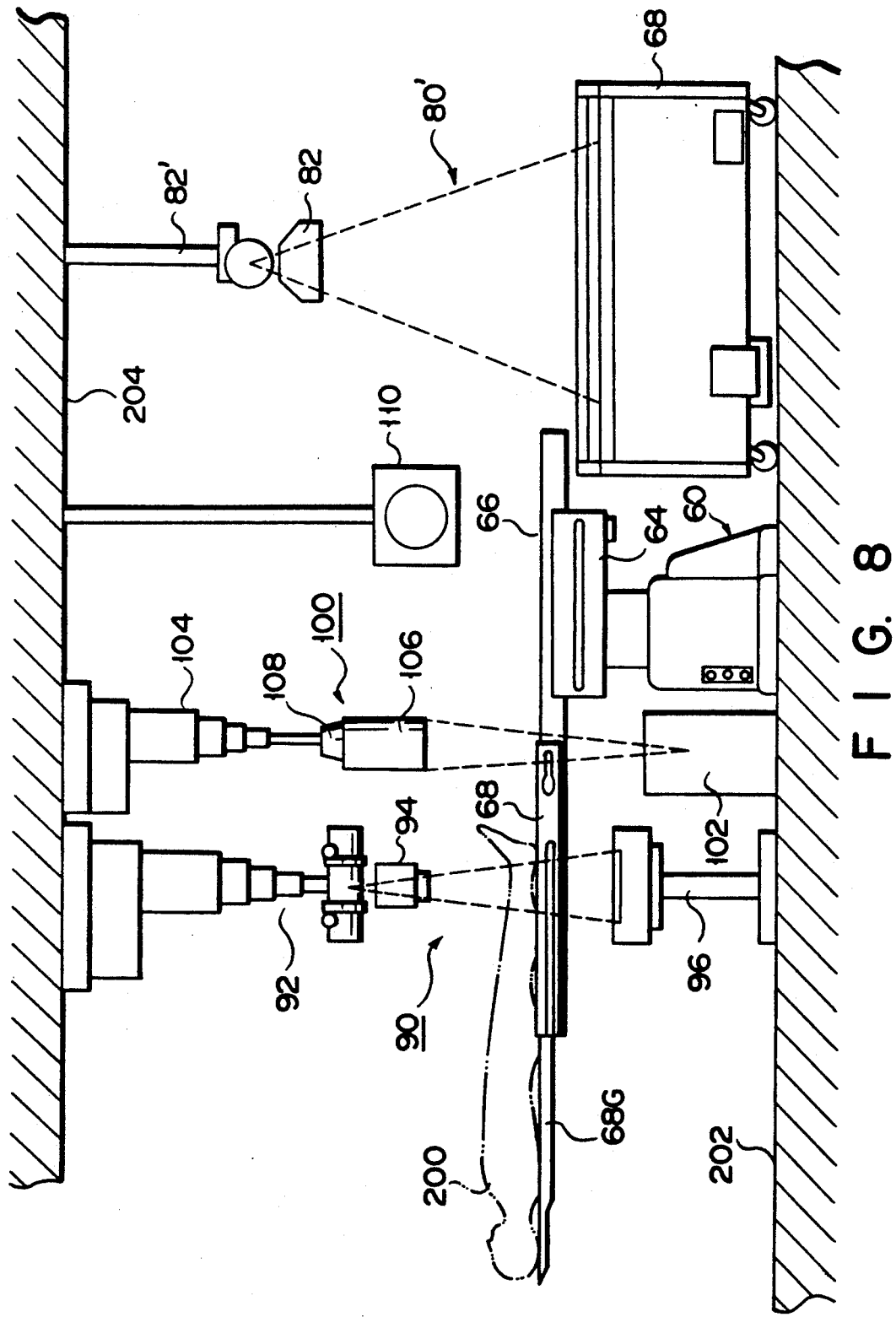
FIG. 8 is a perspective view showing an arrangement of an x-ray photographing apparatus according to another embodiment of the present invention.

An arrangement of an x-ray photographing apparatus according to another embodiment of the present invention will be described below with reference to FIG. 8. In this embodiment, in place of the C arm unit 70 shown in FIGS. 2 and 4, a photographing unit 90 and a fluoroscopic unit 100 are separately arranged. The fluoroscopic unit 100 and the photographing unit 90 are arranged in tandem along the horizontally moving direction of a top plate unit 68 of a catheter bed 60. The fluoroscopic unit 100 is arranged closer to the catheter bed 60 than the photographing unit 90. The photographing unit 90 comprises an x-ray tube support unit 92 fixed to a ceiling 204, an x-ray tube unit 94, and a film changer 96 which is arranged on a floor 202 and has a normal x-ray film stored therein. The fluoroscopic unit 100 comprises an x-ray tube unit 104 arranged on the floor 202, an I.I. support unit 104 fixed to the ceiling 204, an I.I. 106 attached to the I.I. support unit 104, a TV camera 108 fixed to the I.I. 106, and a monitor 110 for displaying a fluoroscopic image obtained by the TV camera 108.

Figure 3:
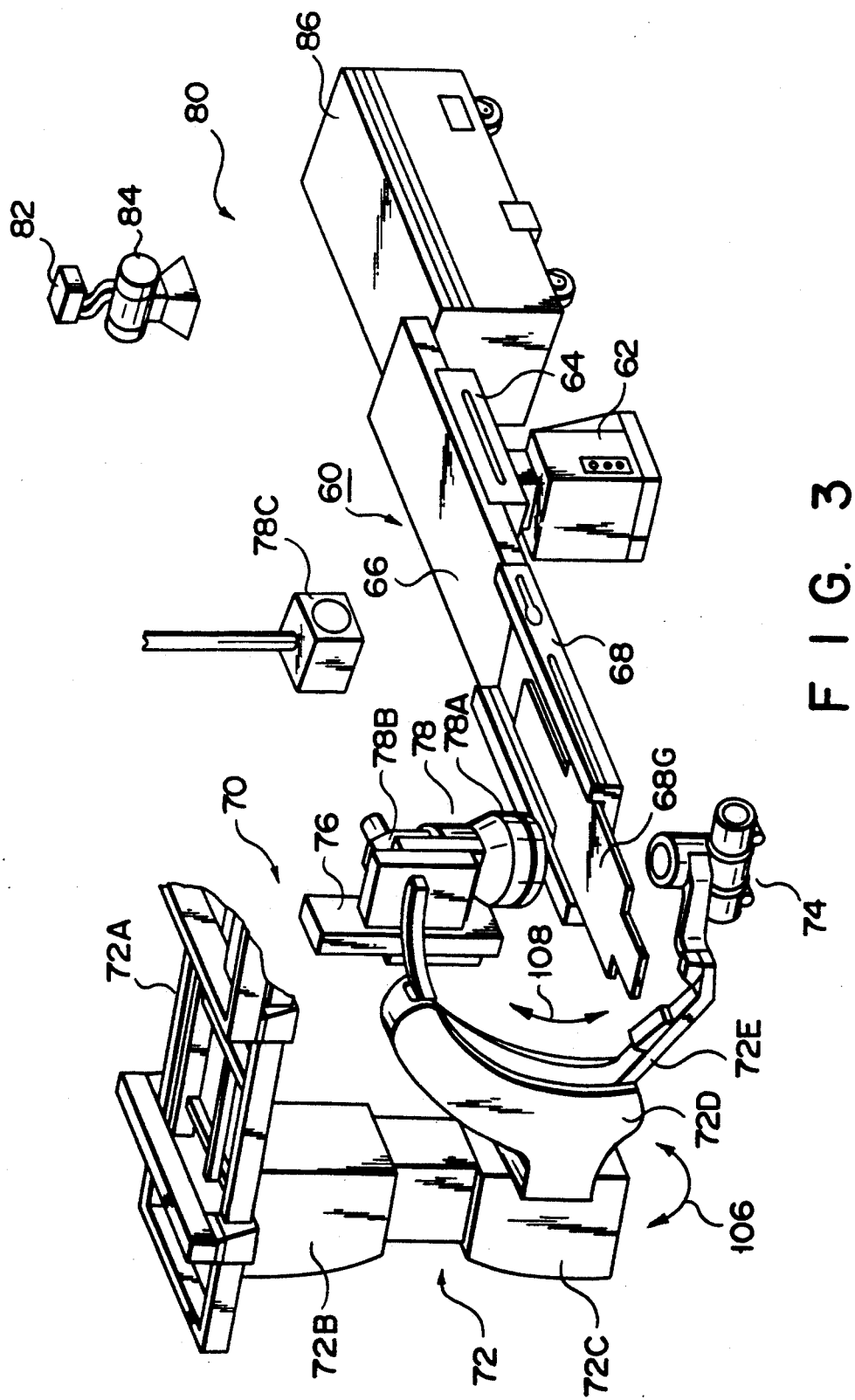
FIG. 3 is a perspective view showing an arrangement of an x-ray photographing apparatus according to the present invention

The x-ray photographing apparatus having the above-described arrangement can be operated in the same manner as described above with reference to the apparatus shown in FIGS. 3 and 4, except that the fluoroscopy and photographing positions of the apparatuses are different from each other.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An x-ray photographing apparatus comprising:
   an arm imaging system comprising:
      an arm unit fixed on a ceiling,
      an x-ray tube unit arranged in said arm unit, and
      an x-ray image detecting unit arranged in said arm unit, and having a film changer for single-shot photography and divisional photography and a fluoroscopic system for fluoroscopy;
   a collective photographic system arranged in tandem with said arm imaging system, and comprising:
      an x-ray tube support arm fixed on said ceiling,
      an x-ray tube supported on said x-ray tube support arm; and
      an elongated film changer placed on a floor, which has an elongated film stored therein;
   a catheter bed system arranged between said arm imaging system and said collective photographing system, and comprising:
      a base arranged on the floor,
      a frame fixed to an upper surface of said base,
      an intermediate moving unit which is arranged on said frame and which can be horizontally moved on said frame, and
      a top plate unit which is arranged on said intermediate moving unit and which can be horizontally moved on said intermediate moving unit;
   a control unit for controlling a movement of said intermediate moving unit of said top plate unit, so as to move in accordance with one of following modes of, a normal movement mode for obtaining said fluoroscopic image and said x-ray film image, a stepping movement mode for divisional photography using said x-ray film, a whole body fluoroscopic image mode, and a collective photographing mode for collective photography using said elongated x-ray film.

2. An x-ray photographing apparatus according to claim 1, wherein said catheter bed system further comprises;
   a first solenoid brake member arranged on both sides of said intermediate moving unit to brake said top plate unit.

3. An x-ray photographing apparatus according to claim 1, wherein said top plate unit of said catheter bed system comprises:
   a top plate frame arranged on said intermediate moving unit;
   a top plate which is arranged on said top plate frame and which can be horizontally moved on said top plate frame; and
   a second solenoid brake member arranged on both sides of said top plate frame to brake said top plate.

4. An x-ray photographing apparatus according to claim 3, further comprising:
   a second motor having a second pinion gear fixed on said intermediate moving unit;
   a second rack gear member which is meshed with said second pinion gear arranged on the lower surface of said top plate unit; and
   a second controller for controlling said second motor.

5. An x-ray photographing apparatus according to claim 3, further comprising:
a control mechanism for controlling a movement of said intermediate moving unit and said top plate unit, so as to move in accordance with one of the following modes of, a normal movement mode for obtaining said fluoroscopic image and said x-ray film image, a stepping movement mode for divisional photography using said x-ray film, a whole body fluoroscopic image mode, and a collective photographing mode for collective photography using said elongated x-ray film.

6. An x-ray photographing apparatus according to claim 3, wherein said catheter bed system further comprises:
a first solenoid brake member arranged on both sides of said intermediate moving unit to brake said top plate unit.

7. An x-ray photographing apparatus according to claim 3, wherein said top plate unit of said catheter bed system comprises:
a top plate frame arranged on said intermediate moving unit;
a top plate which is arranged on said top plate frame and which can be horizontally moved on said top plate flame; and
a second solenoid brake member which is arranged on both sides of said top plate frame to brake said top plate.

8. An x-ray photographing apparatus comprising:
an arm imaging system comprising,
an arm unit fixed on a ceiling,
an x-ray tube unit arranged in said arm unit,
an x-ray image detecting unit arranged in said arm unit, and having a film changer for single-shot photography and divisional photography, and a fluoroscopic system for fluoroscopy;
a collective photographing system arranged in tandem with said arm imaging system, and comprising:
an x-ray tube support arm fixed on said ceiling,
an x-ray tube supported on said x-ray tube support arm, and
an elongated film changer placed on a floor, which has an elongated film stored therein;
a catheter bed system arranged between said arm imaging system and said collective photographing system, and comprising:
a base arranged on the floor,
a frame fixed to an upper surface of said base, wherein said frame is constituted by a flat portion and a vertical wall portion arranged on both sides of said flat portion,
a first set of roller members arranged on both sides of said flat portion of said frame,
a first motor having a first pinion gear fixed to said flat portion of said frame,
a first controller for controlling said first motor,
an intermediate moving unit arranged in an upper part of said flat portion of said frame and which can be horizontally moved on said frame,
an I-shaped rail member which receives said first roller member of said frame arranged on both sides of said intermediate moving unit,
a first rack gear member which is meshed with said first pinion gear arranged on a lower surface of said intermediate moving unit,
a top plate unit which is arranged on said intermediate moving unit and which can be horizontally moved on said intermediate moving unit,
a roller support plate member arranged below both sides of said top plate unit, and
a second roller which is guided by said I-shaped rail member arranged on said roller support plate member.

9. A catheter bed system used for an x-ray photographing apparatus comprising:
a base arranged on a floor;
a frame fixed to an upper surface of said base;
an intermediate moving unit which is arranged on said frame and which can be horizontally moved on said frame;
a top plate unit which is arranged on said intermediate moving unit and which can be horizontally moved on said intermediate moving unit; and
a control unit for controlling movement of said intermediate moving unit and said top plate unit, so as to move in accordance with one of the following modes of, a normal movement mode for obtaining a fluoroscopic image and an x-ray film, a stepping movement mode for divisional photography using said x-ray film, a whole body fluoroscopic image mode, and a collective photographing mode for collective photography using an elongated x-ray film.

10. A catheter bed system used for an x-ray photographing apparatus according to claim 9, further comprising:
a first solenoid brake member arranged on both sides of said intermediate moving unit to brake said top plate unit.

11. A catheter bed system used for an x-ray photographing apparatus according to claim 9, wherein said top plate unit of said catheter bed system comprises:
a top plate frame arranged on said intermediate moving unit;
a top plate arranged on said top plate frame, and which can be horizontally moved on said top plate frame; and
a second solenoid brake member arranged on both sides of said top plate frame to brake said top plate.

12. A catheter bed system used for an x-ray photographing apparatus comprising:
a base arranged on a floor;
a frame fixed to an upper surface of said base, wherein said frame is constituted by a flat portion and a vertical wall portion arranged on both sides of said flat portion;
a first roller member arranged on both sides of said flat portion of said frame;
a first motor having a first pinion gear fixed to said flat portion of said frame;
a first controller for controlling said first motor;
an intermediate moving unit which is arranged in an upper part of said flat portion of said frame, and which can be horizontally moved on said frame;
an I-shaped rail member which receives said first roller member of said frame arranged on both sides of said intermediate moving unit;
a first rack gear member which is meshed with said first pinion gear arranged on a lower surface of said intermediate moving unit;
a top plate unit which is arranged on said intermediate moving unit, and which can be horizontally moved on said intermediate moving unit;

a roller support plate member arranged below both sides of said top plate unit; and a second roller member which is guided by said I-shaped rail member arranged on said roller support plate member.

13. A catheter bed system used for an x-ray photographing apparatus according to claim 12, further comprising:
   a second motor having a second pinion gear fixed on said intermediate moving unit;
   a second rack gear member which is meshed with said second pinion gear and which is arranged on a lower surface of said top plate unit; and
   a second controller for controlling said second motor.

14. A catheter bed system used for an x-ray photographing apparatus according to claim 12, further comprising:
   a control mechanism for controlling a movement of said intermediate moving unit and said top plate unit, so as to move in accordance with one of the following modes of, a normal movement mode for obtaining a fluoroscopic image and an x-ray film image, a stepping movement mode for divisional photography using said x-ray film, a whole body fluoroscopic image mode, and a collective photographing mode for collective photography using said elongated x-ray film.

15. A catheter bed system for an x-ray photographing an x-ray photographing apparatus, according to claim 12, further comprising:
   a first solenoid brake member arranged on both sides of said intermediate moving unit to brake said top plate unit.

16. A catheter bed system used for an x-ray photographing apparatus according to claim 12, wherein said top plate unit of said catheter bed system comprises:
   a top plate frame which is arranged on said intermediate moving unit;
   a top plate which is arranged on said top plate frame, and which can be horizontally moved on said top plate flame; and
   a second solenoid brake member arranged on both sides of said top plate frame to brake said top plate.

* * * * *